(12) United States Patent
Bracke et al.

(10) Patent No.: US 10,342,619 B2
(45) Date of Patent: Jul. 9, 2019

(54) METHOD AND DEVICE FOR DETERMINING THE MECHANICAL AXIS OF A BONE

(75) Inventors: Bert Bracke, Vaterstetten (DE); Christian Brack, Neusäß (DE); Timo Neubauer, Grasbrunn-Neukeferloh (DE); Manuel Millahn, München (DE)

(73) Assignee: Brainlab AG, Munich (DE)

(*) Notice: Subject to any disclaimer, the term of this patent is extended or adjusted under 35 U.S.C. 154(b) by 656 days.

(21) Appl. No.: 14/125,596

(22) PCT Filed: Jun. 15, 2011

(86) PCT No.: PCT/EP2011/059877
§ 371 (c)(1),
(2), (4) Date: Dec. 12, 2013

(87) PCT Pub. No.: WO2012/171555
PCT Pub. Date: Dec. 20, 2012

(65) Prior Publication Data
US 2014/0225999 A1    Aug. 14, 2014

(51) Int. Cl.
*A61B 90/00* (2016.01)
*A61B 34/10* (2016.01)
*A61B 34/20* (2016.01)

(52) U.S. Cl.
CPC ............ *A61B 34/10* (2016.02); *A61B 34/20* (2016.02); *A61B 90/39* (2016.02);
(Continued)

(58) Field of Classification Search
CPC ............ A61B 19/50; A61B 2034/2068; A61B 2034/2057; A61B 2034/2048;
(Continued)

(56) References Cited

U.S. PATENT DOCUMENTS 5,690,635 A * 11/1997 Matsen, III ............ A61B 17/15
606/88
7,559,931 B2    7/2009 Stone
(Continued)

FOREIGN PATENT DOCUMENTS

DE          4225112 C1     12/1993
DE       102004057933      6/2006
(Continued)

OTHER PUBLICATIONS

International Search report for PCT/EP2011/059877 dated Mar. 5, 2012.
(Continued)

*Primary Examiner* — Matthew K Kwan
(74) *Attorney, Agent, or Firm* — Tucker Ellis LLP

(57) ABSTRACT

The present invention relates to a method for determining the mechanical axis of a bone using an electronic device which is rigidly attached to the bone and comprises a video camera, wherein:
  the mechanical axis is determined from the positions of two points which define the mechanical axis;
  the first of the two points is determined as the center of rotation when the bone is pivoted about the first point, the center of rotation being determined from an output signal of the camera which captures a stationary marker device; and
  the second point is the exit point of the mechanical axis on the outer surface at the opposite end of the bone to the first point.

20 Claims, 3 Drawing Sheets

Figures 1A, 1B:
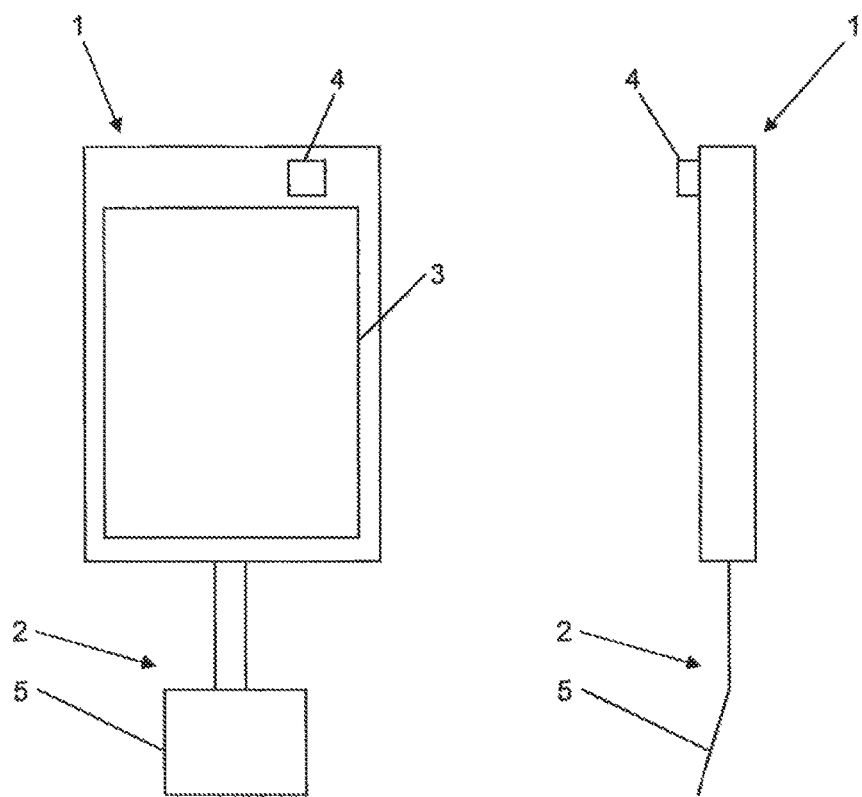

(52) U.S. Cl.
CPC . *A61B 2034/107* (2016.02); *A61B 2034/2048* (2016.02); *A61B 2034/2057* (2016.02); *A61B 2034/2068* (2016.02)

(58) Field of Classification Search
CPC ... A61B 2034/107; A61B 34/10; A61B 34/20; A61B 90/39
USPC .......................................................... 348/77
See application file for complete search history.

(56) References Cited

U.S. PATENT DOCUMENTS

| | | | | |
|---|---|---|---|---|
| 2003/0069591 | A1* | 4/2003 | Carson | A61B 17/154 606/130 |
| 2005/0197569 | A1* | 9/2005 | McCombs | A61B 17/154 600/426 |
| 2006/0004284 | A1 | 1/2006 | Grunschlager et al. | |
| 2007/0117437 | A1 | 5/2007 | Boehnlein et al. | |
| 2008/0030587 | A1* | 2/2008 | Helbing | G06T 5/50 348/208.4 |
| 2010/0100081 | A1* | 4/2010 | Tuma | A61B 17/00 606/1 |
| 2010/0111370 | A1* | 5/2010 | Black | G06K 9/00369 382/111 |
| 2011/0093278 | A1 | 4/2011 | Hutton | |
| 2011/0117025 | A1* | 5/2011 | Dacosta | A61B 5/0059 424/9.6 |
| 2011/0208093 | A1* | 8/2011 | Gross | A61B 5/4528 600/587 |
| 2012/0053594 | A1* | 3/2012 | Pelletier | A61B 34/20 606/102 |

FOREIGN PATENT DOCUMENTS

| | | |
|---|---|---|
| EP | 1806109 A1 | 7/2007 |
| EP | 2179703 A1 | 4/2010 |
| WO | WO 2011020505 A1 | 2/2011 |

OTHER PUBLICATIONS

Brainlab Corporate: "Dash-Computer Assisted Joint Replacement with the iPod touch" XP002669526, http://www.youtube.com/watch?v=pE3xce20Bi8, Feb. 17, 2011.

* cited by examiner

METHOD AND DEVICE FOR DETERMINING THE MECHANICAL AXIS OF A BONE

RELATED APPLICATION DATA

This application is a national phase application of International Application No. PCT/EP2011/059877 filed Jun. 15, 2011 and published in the English language.

The present invention relates to a method and an electronic device for determining the mechanical axis of a bone.

In many medical applications, it is important to know the mechanical axis of a bone. This mechanical axis is important for diagnostic purposes as well as for preparing surgical steps. The mechanical axis can for example be a reference for a cutting plane, preparatory to performing a cut for implanting an artificial replacement. The mechanical axis is particularly important with reference to long bones, such as the femur, tibia, humerus, ulna or radius.

The use of medical navigation systems in image-guided surgery, for example for registering objects such as bones and determining the positions of objects such as medical instruments, is widely known. In a typical medical navigation system, a marker device is attached to an object, and the position—i.e. the location and/or alignment—of the marker device and therefore the object is determined using a tracking unit which tracks the marker device.

Document EP 1 806 109 A1 discloses a method for localising a femur head centre of a knee using only a marker array attached to a tibia. The knee is modelled as a joint having at least one degree of freedom, and a geometric model is used to describe the kinematical behaviour of the joint.

Document EP 2 179 703 A1 discloses a surgical instrument with an integrated display for assisting in image-guided surgery. The instrument carries tracking markings and comprises an integrated inertial sensor system.

Document WO 2011/020505 A1 discloses a portable unit comprising a medical instrument, a tracking system including a sensor system, a medical navigation system including a display and a moving sensor.

Document U.S. Pat. No. 7,559,931 B2 discloses a surgical orientation system for assisting a surgeon in obtaining a correct orientation of an acetabular prosthetic socket in a patient's acetabulum during a total hip arthroplasty procedure. The system identifies the orientation of an instrument with respect to a previously set plane of the acetabulum using accelerometers or other sensors for providing linear positioning information.

Document DE 10 2004 057 933 A1 discloses a method and an apparatus for navigating and positioning an object relative to a patient using a three-dimensional inertial sensor system.

Document DE 42 25 112 C1 discloses an apparatus for determining the position of an instrument relative to an object to be treated. The apparatus uses an inertial sensor system and an optical detection system.

It is an object of the present invention to provide a method and device for determining the mechanical axis of a bone at low cost and with as little surgical intervention as possible.

This problem is solved by the independent claims. Preferred embodiments are defined in the dependent claims.

The present invention relates to a method for determining the mechanical axis of a bone using an electronic device which is rigidly attached to the bone and comprises a video camera. The mechanical axis is determined from the positions of two points which define the axis. The first of the two points is determined as the centre of rotation when the bone is pivoted about the first point, the centre of rotation being determined from an output signal of the camera which captures a stationary marker. The second point is the exit point of the mechanical axis on the outer surface at the opposite end of the bone to the first point. This second point is easily identified by the skilled person, depending on the type of bone, from his general knowledge.

If the bone is a femur, then the first point is the centre of the femoral head and the second point is the deepest point in the intercondylar notch (fossa intercondylaris). In the case of a tibia, the first point is the centre of the talus and the second point is the intercondylar eminence (eminentia intercondylaris). The definitions are similar, in particular regarding the second point, for other long bones and are well-known to the skilled person.

Depending on the type of bone, the mechanical axis may not coincide with the anatomical axis. The anatomical axis is the axis of the diaphysis. Taking the femur as an example, the angle between the mechanical axis and the anatomical axis is typically around 7 degrees.

As indicated above, the first point is typically the centre of a joint. This joint can allow relative movement in two rotational dimensions, such as a ball joint or a saddle joint, or in one rotational dimension, such as a hinge joint. In order to determine the first point, the bone including the rigidly attached electronic device is pivoted about the centre of rotation. If the joint allows one rotational degree of freedom, then the electronic device moves along a circular arc. If the joint allows two rotational degrees of freedom, then the electronic device moves over a spherical surface. During the movement, the camera of the electronic device captures the stationary marker device.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The markers can also however be passive, i.e. can for example reflect electromagnetic radiation in the infrared, visible and/or ultraviolet spectral range. To this end, the markers can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker as used in the present invention is preferably a spherical body which reflects light in the visible spectrum. A marker preferably also comprises a pattern, such as a rhomb, a lune, a part of a lune or more than one of these regions. Such a pattern simplifies the detection and alignment of the marker.

A marker device can for example be a reference star or a pointer or one or more (individual) markers in a predetermined spatial relationship. A marker device comprises one, two, three or more markers in a predetermined spatial relationship. This predetermined spatial relationship is in particular known to a navigation system and for example stored in a computer of the navigation system.

Preferably, the marker device comprises three or more markers, in particular four or five markers.

When the bone is pivoted about the first point, the two-dimensional image of the marker device changes. This is caused by the change in the viewing angle of the camera which results in a change in the projection of the markers of the marker device. The output signal, i.e. the captured image, of the camera for different positions of the electronic device can be analysed in a known manner in order to calculate the respective positions of the electronic device. As outlined above, all the positions are located on a circular arc or a spherical surface. From these positions, it is possible to calculate the centre of the arc or sphere, respectively, as the centre of rotation and therefore the first point.

Due to inaccuracies which might occur when the positions of the electronic device are determined, the determined positions might not exactly lie on the circular arc or on the sphere. One option is then to use a virtual arc or sphere which approximates the actual arc or sphere on which the electronic device moves. The virtual arc or sphere may be fitted to the determined positions using an appropriate algorithm such as a least-squares approach.

The position of the first point is preferably determined in a co-ordinate system, preferably a Cartesian co-ordinate system, which relates to the electronic device. In addition or as an alternative, the position of the first point can be determined in a stationary co-ordinate system which relates for example to the stationary marker device. In this document, such a co-ordinate system is referred to as a global co-ordinate system. The position of the first point in the device-centred co-ordinate system can be transformed into a position in the global co-ordinate system if the position, i.e. the location and/or alignment, of the electronic device in the global co-ordinate system is known. One way of determining the position of the electronic device is to analyse an image of the stationary marker device captured using the camera of the electronic device.

The second point defining the mechanical axis of the bone is located at the opposite end of the bone to the end at which the first point is located. The second point is the exit point of the mechanical axis at the outer surface of the bone. For each kind of bone, there is a known medical definition of the second point.

The second point is a point on the surface of the bone which is defined by the outer structure or surface of the bone. It is in particular a landmark of the bone or is defined in relation to one or more landmarks of the bone.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Other landmarks include one defined by the rim of the acetabulum, for instance by the centre of the rim. In another example, a landmark is represented by the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part.

There are several ways of determining the position of the second point. One is to determine the position of the second point from the position of at least one point on the surface of the bone which is sampled using a pointer which comprises a marker device, said marker device being detected using the camera of the electronic device.

A tip of the pointer is brought into contact with the point to be sampled, and an image of the marker device attached to the pointer is captured using the camera. From the captured image, it is possible to calculate the position of the marker device on the pointer. From the calculated position of the marker device and the known positional relationship between the marker device and the tip of the pointer, it is possible to calculate the position of the tip and therefore the position of the sampled point. The position of the second point is preferably calculated in the co-ordinate system which relates to the electronic device. In addition or as an alternative, however, the position of the second point can be determined in the global co-ordinate system.

Preferably, the sampled point is the second point. However, there may be situations in which it is not possible to directly sample the second point using the pointer. In this case, one or preferably more than one, in particular two or three, points other than the second point are sampled on the surface of the bone, and the position of the second point is calculated from the positions of the sampled points. The sampled points are preferably landmarks of the bone.

In one embodiment, the position of the second point is calculated from the positions of the sampled points according to a predetermined calculation rule which incorporates the structure of the bone. In another embodiment, a generic model of the bone is matched, or morphed, to the sampled points. This means that the generic model, which can be a grid model, is deformed such that points of the generic model which correspond to the sampled points are matched to the positions of the sampled points. In the generic model, the position of the second point is provided. During matching, the position of the second point within the generic model is also transformed and subsequently used as the position of the second point.

In one alternative to measuring or calculating the position of the second point using a pointer, the electronic device is positioned relative to the bone using a template such that the second point is in a predefined spatial relationship with respect to the electronic device. In other words, a template, such as a gauge or a setting jig, is held on the bone such that it is in a defined spatial relationship with respect to the second point. The electronic device is then aligned relative to the template such that there is a predefined spatial relationship between the template and the electronic device. This means that there is then also a defined spatial relationship between the electronic device and the second point. This in turn means that the position of the second point relative to the electronic device, and therefore in a co-ordinate system relating to the electronic device, is known. Measuring the position of the second point can thus be omitted.

The template is preferably self-centring on the bone, for example by having the inverse shape of at least a part of the surface of the bone. When designed in this way, the template is automatically guided to the correct position relative to the second point.

In one embodiment, the template can be adapted, for example to the size of the bone. The size of the bone can be measured, for example in an x-ray image of the bone or an image created by any other suitable modality. The length of the bone is preferably used as a measure of the size of the bone. Making the template adaptable is particularly useful if the template is self-centring.

Optionally, the template points to the second point. The template can for example comprise an arrow, the tip of which ends at the second point. This arrow can be used to place the template. If the template is self-centring, then the alignment of the electronic device with respect to the second point can be validated by pointing the tip of a pointer to the tip of the arrow on the template and determining the position of the second point in the co-ordinate system of the electronic device, as explained above.

In another alternative, the position of the second point relative to the electronic device can be measured, for example using a ruler. The measured distances in up to three translational dimensions are then manually inputted, for example to the electronic device or an external control unit.

In a preferred embodiment, the electronic device also comprises at least one inertial sensor. An inertial sensor can comprise an accelerometer for detecting a linear acceleration and/or a gyroscope for determining an angular velocity. Using the inertial sensor, and in particular an arrangement of three orthogonal inertial sensors, the movement of the electronic device can be determined in addition to or instead of using the camera which captures the stationary marker device. The output signal of the at least one inertial sensor is preferably used to determine the first point. The at least one inertial sensor is in particular used to determine the positions of the electronic device on the circular arc or spherical surface, respectively, and subsequently the centre of rotation.

Preferably, the output signal of the at least one inertial sensor is used to determine the first point if the stationary marker is not captured by the camera. This can occur if there is an obstacle between the camera and the stationary marker device or if the bone is pivoted into a position in which the stationary marker device is not within the field of view of the camera. In this case, the position of the electronic device would no longer be able to be tracked. By using the at least one inertial sensor, it is possible to compensate for the loss of tracking by the camera. However, the output signal of the at least one inertial sensor can also be used concurrently with the output signal of the camera, to increase the accuracy with which the position of the electronic device is detected. In another alternative, the positions of the electronic device on the arc or spherical surface are detected only from the output signal of the at least one inertial sensor and not from the output signal of the camera.

The electronic device optionally also comprises a gravity sensor. The output signal of the gravity sensor represents the direction of gravity, represented in particular by a vector. The output signal of the gravity sensor can also be used to determine the position of the electronic device and subsequently the position of the first point.

Using the method described above, it is possible to determine the mechanical axis in the co-ordinate system of the electronic device or a global co-ordinate system. However, a relationship with respect to the bone has not yet been established. In particular, there is an ambiguity in the rotational alignment of the bone about the mechanical axis. One way of establishing the relationship between the bone and the electronic device is to sample a landmark, preferably two or more landmarks, and to determine the orientation of the bone in the co-ordinate system of the electronic device or in the global co-ordinate system from the positions of the sampled landmarks.

In a preferred embodiment, the electronic device is attached to the bone such that a defined direction of the device coincides with a defined direction of the bone. The defined direction of the device is preferably indicated on the surface of the device or a holding device which is used to attach the electronic device to the bone. This defined direction preferably coincides with one axis of the Cartesian co-ordinate system of the electronic device. The defined direction of the bone is preferably a sagittal direction, i.e. an AP (anterior-posterior) direction. If the defined direction of the bone is the sagittal direction and the holding device of the electronic device does not allow the defined direction of the electronic device to be aligned in the sagittal direction, then the electronic device is attached to the bone such that the projection of the defined direction of the electronic device into the transverse plane coincides with the sagittal direction. The spatial relationship between the bone and the electronic device can then be determined from the geometry of the holding device, as explained below. In more general terms, if the holding device of the electronic device does not allow the defined direction of the electronic device to be aligned with the defined direction of the bone, then the electronic device is aligned such that the projection of the defined direction of the electronic device into a suitable plane, wherein the defined direction of the bone lies within this plane, is aligned with the defined direction of the bone.

In a preferred embodiment, the electronic device is attached to a cutting block which is pre-attached to the bone. The electronic device or a holding device of the electronic device is in particular inserted into the slit of the cutting block and then locked in place, preferably after the electronic device has been aligned relative to the bone. In this embodiment, the holding means comprises a sheet or a sheet-like member which is inserted into the slit of the cutting block. In this document, the term "sheet" always also encompasses the meaning of a sheet-like member. The sheet is preferably smaller than the slit, such that a relative movement of the sheet in the slit is possible in two translational dimensions which lie within the cutting plane defined by the slit. A rotational movement of the sheet within the slit is also possible about an axis which is perpendicular to the cutting plane. This design enables the electronic device to be aligned relative to the cutting block and therefore relative to the bone.

The present invention also relates to a method for spatially calibrating an electronic device and a holding device with a sheet to which the electronic device is rigidly attached. Throughout this document, the expression "rigidly attached" is understood to mean that no relative movement is possible between two components which are rigidly attached. This includes both rotational and translational movements.

In a first step, the sheet—which is rigidly attached to the electronic device—is inserted into a probe slit. The probe slit is designed such that it holds the sheet in a well-defined and unique position. The camera of the electronic device then captures an image of at least one marker device, wherein the spatial relationship between the probe slit and the captured marker device is known and for example stored in the electronic device. From the captured image, i.e. the output signal of the camera, it is possible to calculate the position of the captured marker device relative to the camera, in particular the lens of the camera, in a known manner. Since the spatial relationship between the captured marker device and the sheet is known, the spatial relationship between the camera, and therefore the electronic device, and the sheet can be calculated. This calculated spatial relationship is then stored, for example in the electronic device or in a database which can be accessed when the electronic device is used to determine the mechanical axis of a bone.

The present invention also relates to a device for spatially calibrating an electronic device and a sheet of a holding device which is rigidly attached to the electronic device. The calibration device comprises a probe slit, which can receive the sheet of the holding device in a predefined position, and at least one marker device with a known spatial relationship relative to the probe slit.

The present invention also relates to a method for validating a cutting plane in preparation for a surgical step of cutting into a bone. A part of the bone is usually cut off in order to be replaced by an implant, in particular as a part of an artificial joint. In order to be able to correctly position the implant, it is essential to align the cutting plane in which the bone is cut relative to the bone to a high level of accuracy, such as 1° to 2°. In order to perform the cut, a cutting block is rigidly attached to the bone. The cutting block comprises a base portion which is rigidly attached to the bone, and a slit for guiding a sawing tool which is used to perform the cut. Typical cutting blocks are adjustable such that the cutting plane can be fine-tuned relative to the base portion. The cutting block is typically adjustable in two rotational dimensions.

As outlined above, it is important to validate the cutting plane before the actual cut is performed. In order to validate the cutting plane, the mechanical axis of the bone is determined as described above. The position of the cutting plane as defined by the slit in the cutting block is then determined from the position of the electronic device, and therefore the position of the sheet of the holding device which is locked in the slit, relative to the mechanical axis. The determined cutting plane is then compared to a desired cutting plane. If the determined cutting plane and the desired cutting plane are within a predetermined tolerance of each other, the cut can be performed. Otherwise, the cutting block is adjusted and the cutting plane is validated again.

The method described above requires the relevant parts of the bone to be exposed beforehand and the electronic device, or the cutting block, to be attached to the bone beforehand. The steps of determining the mechanical axis or validating the cutting plane do not themselves include any surgical step. Said surgical steps are carried out before the methods described above are applied. The surgical steps are preferably not part of the present invention.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular any kind of electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

A complete surgical procedure comprises the step of exposing at least a part of the bone and rigidly attaching the electronic device, or, as applicable, at least a cutting block, to the bone before the mechanical axis is determined. The complete surgical procedure can also comprise subsequent steps such as performing a cut.

In a modification of the method described above, a stationary camera is used to acquire the positions of landmarks on the bone in a global co-ordinate system relating to the stationary camera. The position of the cutting plane can be acquired by determining the position of a marker device attached to the slit, using the stationary camera. If the cutting block is adjusted, the marker device in the slit moves relative to the stationary camera. It is therefore not possible to distinguish whether the slit of the cutting block has moved due to an adjustment of the cutting block or a movement of the patient and therefore the bone. In this modification of the invention, the electronic device is rigidly attached to the bone, and movement of the bone is tracked using the at least one inertial sensor of the electronic device. With the additional information from the at least one inertial sensor, the portion of the movement of the marker device in the slit, and therefore of the slit, which is caused by a movement of the bone can be computationally eliminated, such that the actual adjustment of the cutting slit can be tracked. The electronic device is preferably rigidly attached to a base of the cutting block which is rigidly attached to the bone. This avoids the need to cause further damage to the bone by additional attaching means such as screws for attaching the electronic device to the bone.

In another embodiment of this modification, a desired cutting plane position can be approached by fixing the bone and using the at least one inertial sensor of the electronic device, which is attached to the slit of the cutting block, to track the relative movement of the slit starting from an acquired initial cutting plane position.

The present invention also relates to an electronic device comprising a video camera and at least one inertial sensor. The electronic device comprises means, for example a holding device, for rigidly attaching the device to the bone. The electronic device also comprises a control unit which is configured to carry out the method steps of the methods for determining the mechanical axis of the bone or the method for validating a cutting plane as described above.

The camera, the at least one inertial sensor and the control unit are preferably integrated into a common housing. The electronic device is then an integrated device which can be handled easily and can be provided at low cost. All the processing steps needed in order to carry out the method are performed in a single integrated unit. Alternatively, the camera and the at least one inertial sensor are provided in a first housing, and the control unit is provided in a second housing which is separate from the first housing. The electronic device also comprises data transfer means for transferring data from the camera and the at least one inertial sensor to the control unit. The data transfer means is preferably a Bluetooth communication unit. This is particularly useful if a processor of the electronic device is too slow to carry out the calculations for performing the described methods.

The electronic device preferably also comprises a display unit. The display unit is preferably provided in the common housing or in the first housing if the control unit is provided in a separate, second housing. In this configuration, the display unit is located in a workspace and can be easily observed, for example if the cutting block is adjusted.

The control unit is preferably configured to provide display data to the display unit which represent the determined cutting plane. The display data preferably also represent the desired cutting plane. The determined cutting plane and, as applicable, the desired cutting plane can be graphically displayed, for example in a graphical representation of the bone, and/or as numerical values. Additionally or alternatively, the display data can represent adjustment data which indicate how the cutting block is to be adjusted such that the cutting plane matches the desired cutting plane to a predetermined level of accuracy. If the display unit and the control unit are not located in the same housing, then the display data are transmitted from the control unit to the display unit, for example using the data transfer means described above.

The present invention also relates to a medical navigation system comprising an electronic device as described above and a stationary marker device.

The present invention also relates to a computer program which, when running on a computer or loaded onto a computer, causes the computer to perform a method as described above and/or to a computer program storage medium on which the program is stored (in particular in a non-transitory form) and/or to a computer on which the program is running or into the memory of which the program is loaded.

Within the framework of the invention, computer program elements can be embodied by hardware and/or software (this includes firmware, resident software, micro-code, etc.). Within the framework of the invention, computer program elements can take the form of a computer program product which can be embodied by a computer-usable and/or in particular computer-readable data storage medium comprising computer-usable and/or in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention. Within the framework of the present invention, a computer-usable and/or in particular computer-readable data storage medium can be any data storage medium which can include, store, communicate, propagate or transport the program for use on or in connection with the instruction-executing system, apparatus or device. The computer-usable and/or in particular computer-readable data storage medium can for example be, but is not limited to, an electronic, magnetic, optical, electromagnetic, infrared or semiconductor system, apparatus or device or a medium of propagation such as for example the Internet. The computer-usable and/or computer-readable data storage medium could even for example be paper or another suitable medium onto which the program is printed, since the program could be electronically captured, for example by optically scanning the paper or other suitable medium, and then compiled, interpreted or otherwise processed in a suitable manner.

Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention also relates to the use of an electronic consumer device comprising a video camera and at least one inertial sensor as a sensor device in a medical navigation system. Electronic consumer devices are off-the-shelf devices intended for everyday use, for example in the fields of communications or entertainment. Examples of such electronic consumer devices include the iPod produced by Apple Inc. or smartphones, i.e. portable telephones with enhanced functionality. Such electronic consumer devices are widespread and only need a suitable software program in order to be used in a medical navigation application. If the processor of the electronic consumer device is fast enough, then all the necessary processing tasks, including tracking the marker device in the image captured by the camera, calculating the first and second points and calculating the mechanical axis and/or the cutting plane, can be performed by the device without the need of any additional computer hardware.

Different advantageous features described herein can be combined in accordance with the invention wherever this is technically sensible and feasible. In particular, a feature of one embodiment which supplements another embodiment with an additional function can be added to said other embodiment. Features which are not essential to the essence of the present invention can also be omitted from the described embodiments.

Figure 2:
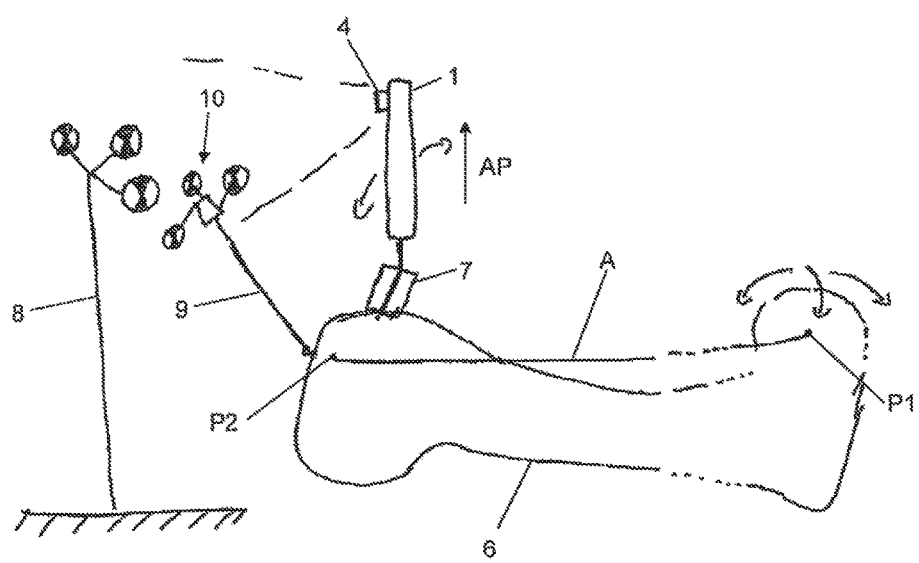

A preferred embodiment of the present invention shall now be explained with reference to the accompanying figures, which show:

FIG. 1 two views of an electronic device with a holding device;

FIG. 2 the electronic device attached to a bone; and

Figure 3:
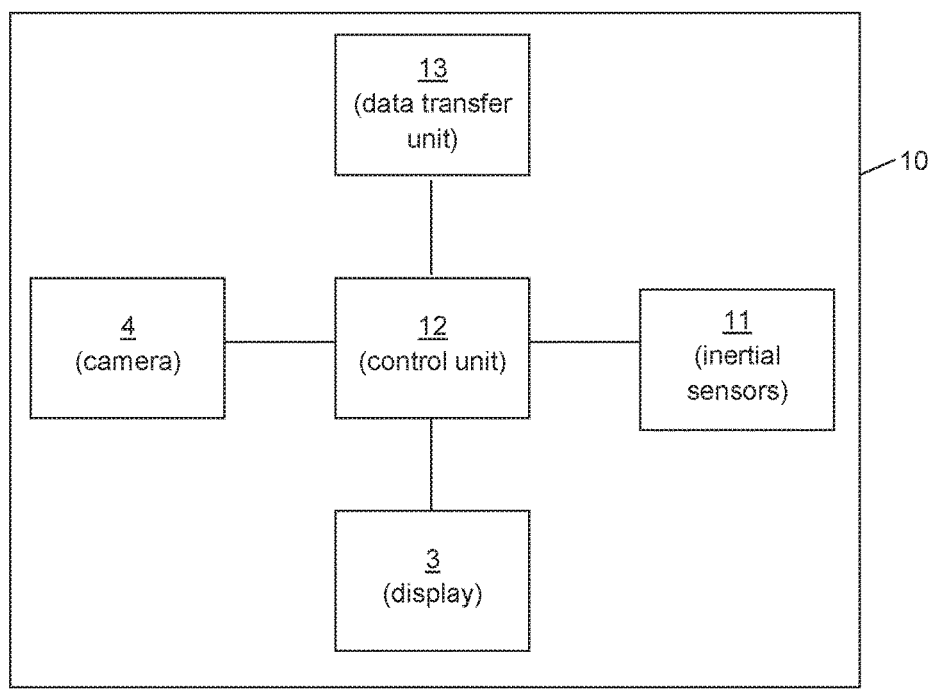

FIG. 3 a schematic representation of the structure of the electronic device.

FIGS. 1A and 1B show a front view and a side view, respectively, of an electronic device 1. In this embodiment, the electronic device 1 is an iPod produced by Apple Inc., but, could also be any other suitable device. The electronic device 1 comprises a display 3 and a camera 4 which is receptive to light in the visible spectrum.

The electronic device 1 is rigidly attached to a holding device 2. At one end, the holding device 2 is attached to the electronic device 1. At the other end, the holding device 2 comprises a sheet 5. As can be seen from FIG. 1B, the sheet 5 is angled relative to the vertical axis of the electronic device 1.

FIG. 2 shows a bone 6 exhibiting a mechanical axis A which is to be determined. The mechanical axis A is defined by the points P1 and P2. In the present example, the bone 6 is a femur. The first point P1 is the centre of the femoral head, and the point P2 is the deepest point of the intercondylar notch.

An adjustable cutting block 7 comprises a base portion which is rigidly attached to the bone 6, and a slit which exhibits an orientation which can be adjusted in two rotational dimensions relative to the base portion of the cutting block 7.

A Cartesian co-ordinate system is defined in relation to the electronic device 1. The first axis corresponds to the vertical axis of the electronic device 1 and runs vertically in the drawing plane of FIGS. 1A and 1B. The second axis runs horizontally in the drawing plane of FIG. 1A, while the third axis is perpendicular to the drawing plane of FIG. 1A.

In a first step of the method, the sheet 5 of the holding device 2 is inserted into the slit of the cutting block 7. By moving the sheet 5 within the slit, the electronic device 1 is aligned such that the vertical axis of the electronic device 1 is aligned with the sagittal direction of the bone 6. This sagittal direction is indicated by the arrow AP (anterior-posterior) in FIG. 2. Once the electronic device 1 is aligned correctly, the sheet 5 is locked in place in the slit of the cutting block 7 such that the electronic device 1 is then rigidly attached to the bone 6.

In a second step, the bone 6 is pivoted about the first point P1. Since the femoral head is part of a ball joint, every point of the bone, the cutting block 7 and the electronic device 1 can move over a spherical surface centred at the point P1. During this movement, the camera 4 of the electronic device 1 repeatedly captures images of a stationary marker device 8. The stationary marker device 8 is stationary with respect to the environment of the bone 6, for example stationary with respect to a room such as an operating theatre in which the bone 6 is situated.

In FIG. 2, the marker device 8 is shown to comprise three marker spheres which exhibit an optical pattern and reflect light in the visible spectrum. The markers of the marker device 8 are arranged in a fixed and known spatial relationship. This spatial relationship of the markers of the marker device 8 is also referred to as a geometric structure or geometric information. In accordance with the angle of view of the camera onto the markers, the captured image is indicative of the viewing angle and the distance between the camera 4 and the marker device 8. The position of the camera 4, and therefore the electronic device 1, relative to the marker device 8 is calculated in the co-ordinate system of the electronic device 1 from the output image of the camera 4.

As outlined above, the positions are located on a spherical surface. A plurality of positions on the spherical surface are calculated from the position of the camera 4 relative to the marker device 8. The centre of the spherical surface and therefore the first point P1 is calculated from said plurality of positions.

In a third step, the tip of a pointer 9 is brought into contact with the second point P2. A marker device 10, which comprises markers in a known geometry and is rigidly attached to the pointer 9, is captured by the camera 4. The spatial position, i.e. location and alignment, of the marker device 10 is calculated by analysing the output image of the camera 4 and taking into account the known geometry of the markers of the marker device 10. Since the spatial relationship between the marker 10 and the tip of the pointer 9 is known, the position of the point P2 which corresponds to the position of the tip of the pointer 9 can be calculated in the co-ordinate system of the electronic device 1.

Since the positions of both the points P1 and P2 are then known in the co-ordinate system of the electronic device 1, the mechanical axis A of the bone 6 can be calculated as the straight line running through the points P1 and P2.

Due to the known spatial relationship between the electronic device 1 and the sheet 5, and therefore the slit of the cutting block 7, the angle between the cutting plane defined by the slit and the mechanical axis A can be calculated. Since the vertical axis of the electronic device 1 is in alignment with the sagittal direction of the bone, the position (location and/or rotational alignment) of the cutting plane can be unambiguously calculated from the angle between the cutting plane and the mechanical axis A.

The determined cutting plane relative to the bone 6 is displayed on the display 3, either graphically or as numerical values or as a combination of both. The desired cutting plane is preferably also displayed, for comparison. It is then possible to judge, from the displayed information, whether or not the actual cutting plane matches the desired cutting plane to the required level of accuracy. Preferably, the electronic device 1 makes this comparison and displays the result of the comparison on the display 3. If the alignment of the cutting plane is not correct, the electronic device 1 optionally displays instructions as to how to adjust the cutting block 7, on the display 3.

FIG. 3 shows a schematic diagram of the electronic device 1. The electronic device 1 comprises a control unit 12 which is connected to the display 3, the camera 4, three inertial sensors 11 and an optional data transfer unit 13. The control unit 12, which is for example a central processing unit, analyses the output signal of the camera 4 and determines the positions of the first point P1 and the second point P2. The control unit 12 also provides the display 3 with display data to be displayed. The control unit 12 preferably comprises a storage unit such as a memory. This memory holds the instructions performed by the control unit 12 and optionally also data such as the geometric structure of the marker devices 8 and 10 and the spatial relationship between the electronic device 1 and the sheet 5 of the holding device 2.

The control unit 12 can optionally transfer the calculated data, such as the position of the mechanical axis A or the cutting plane, to an external device via the optional data transfer unit 13. The control unit 12 can optionally also receive information such as geometric information regarding the marker devices 8 and 10 or the spatial relationship between the electronic device 1 and the sheet 5, via the data transfer unit 13.

The three inertial sensors 11 each comprise an accelerometer and a gyroscope. Each inertial sensor is configured to detect a movement in one of three orthogonal translational and rotational dimensions. The output signals of the inertial sensors 11 are used by the control unit 12 to determine the positions of the electronic device 1 on the spherical surface when the bone is pivoted about the first point P1, at least when a calculation of the position from the output signal of the camera is not possible, for example when there is an obstacle between the camera 4 and the marker device 8 or the marker device 8 is not within the field of view of the camera 4. The control unit 12 can optionally use the output signals of both the camera 4 and the inertial sensors 11 to determine the position of the electronic device 1.

The configuration described in the preferred embodiment of the present invention is not exhaustive. The electronic device 1 can be directly attached to the bone 6 and not via the cutting block 7. The marker devices 8 and 10 can and preferably do have more than three markers. Instead of sampling the position of the second point P2, the electronic device 1 can be attached to the bone 6 such that the second point P2 is in a defined position relative to the electronic device 1. This can be achieved by placing a template on the bone 6 and aligning the electronic device 1 with the aid of the template.

The invention claimed is:

1. A method for determining a mechanical axis of a bone of an associated patient, the bone having a surface, a part of the surface of the bone having a shape, the method comprising:
providing a template having a surface adapted to the shape of the part of the surface of the bone of the associated patient, wherein the surface of the template has an inverse shape of the shape of the part of the surface of the bone of the associated patient;
positioning the template in a predefined spatial relationship relative to the bone by guiding the surface of the template having the inverse shape of the shape of the part of the surface of the bone onto the part of the surface of the bone having the shape, the template when positioned on the part of the surface of the bone having the shape in the predefined spatial relationship relative to the bone defining, relative to the template, a second point of two points defining the mechanical axis of the bone;
providing a defined spatial relationship between a portable consumer electronic device having a camera and the second point of the two points defining the mechanical axis of the bone by positioning the portable consumer electronic device in aligned contact with the template positioned in the predefined spatial relationship relative to the bone, wherein the portable consumer electronic device positioned in the aligned contact with the template positioned in the predefined spatial relationship relative to the bone defines the second point in a reference frame of the portable consumer electronic device; and
determining the first point of the two points defining the mechanical axis of the bone in the reference frame of the electronic device by:
pivoting the bone with the template being positioned on the bone, and with the portable consumer electronic device being in the aligned contact with the template;
during the pivoting and with the template being positioned on the bone and with the portable consumer electronic device being in the aligned contact with the template, capturing via the camera a plurality of images of an associated stationary marker device;
determining a center of rotation of the pivoting of the bone based on the plurality of images of the associated stationary device captured during the pivoting; and
determining the first point of the two points in the reference frame of the portable consumer electronic device as the determined center of rotation,
wherein the two points defining the mechanical axis of the bone comprise the determined first point and the defined second point.

2. The method of claim 1, further comprising:
determining the position of the second point from the position of at least one point on the bone which is sampled using an associated pointer which comprises a marker device; and
detecting said marker device using the video camera of the portable consumer electronic device.

3. The method of claim 1, wherein the determining the first point of the two points defining the mechanical axis comprises using an output signal of at least one inertial sensor of the portable consumer electronic device.

4. The method of claim 3, further comprising:
using the output signal of the at least one inertial sensor to determine the first point responsive to the stationary marker device being not captured by the camera.

5. The method of claim 1, further comprising:
attaching the portable consumer electronic device to the bone such that a defined direction of the electronic device coincides with a defined direction of the bone.

6. The method of claim 1, further comprising:
pre-attaching an associated cutting block to the bone; and
attaching the portable consumer electronic device to the associated cutting block which is pre-attached to the bone.

7. The method of claim 6, further comprising validating a cutting plane in preparation of a surgical step of cutting into the bone by:
determining a position of a cutting plane as defined by a slit in the associated cutting block from the position of the portable consumer electronic device relative to the mechanical axis, and comparing the determined position of the cutting plane with a desired cutting plane.

8. The method of claim 1, further comprising exposing at least a part of the bone having the shape and rigidly attaching the portable consumer electronic device to the exposed at least a part of the bone before the first point of the mechanical axis is determined.

9. The method according to claim 1, further comprising:
self-centering the template on the bone by guiding the template, using the inverse shape of the at least a part of the surface of the bone, to a desired position.

10. The method according to claim 1, wherein the positioning the associated template relative to the bone comprises:
defining the second point by the template as an exit point of the mechanical axis on an outer surface of the bone at an end of the bone opposite of the first point.

11. The method according to claim 1, wherein:
the positioning the template relative to the bone comprises attaching the template with the bone thereby defining the second point of the two points defining the mechanical axis of the bone; and
the aligning the electronic device with the template comprises attaching the electronic device with the template thereby providing the defined spatial relationship between the electronic device and the second point.

12. The method of claim 1, wherein:
the positioning the template in the predefined spatial relationship relative to the bone by guiding the surface of the template having the inverse shape of the shape of the part of the surface of the bone onto the part of the surface of the bone having the shape comprises:
placing the surface of the template having the inverse shape of the shape of the part of the surface of the bone into engagement with the part of the surface of the bone having the shape.

13. The method of claim 1, wherein:
the aligning the electronic device with the template comprises:
attaching the electronic device to the template.

14. A system for determining a mechanical axis of a bone of an associated patient, the bone having a surface, a part of the surface of the bone having a shape, the system comprising:
a portable consumer electronic device comprising:
a camera;
a memory device; and a control unit comprising an embedded processor in operative communication with the camera and the memory, the control unit being operable to determine by the processor executing a computer program stored in the memory device a mechanical axis of the bone of the associated patient from positions of two points that define the mechanical axis; and a template rigidly attaching the portable consumer electronic device with the bone of the associated patient, the template having a surface inversely adapted to the shape of the part of the surface of the bone of the associated patient held in a predetermined spatial relationship on the part of the surface of the bone having the shape, and the portable consumer electronic device being held by the template in a predefined relationship with respect to the associated bone, wherein the control unit determines by the processor executing the computer program stored in the memory device, from an output signal of the camera, a first point of the two points that define the mechanical axis as a center of rotation in a reference frame of the portable consumer electronic device when the associated bone is pivoted about the center of rotation, the output signal being generated by the camera capturing a plurality of images of an associated stationary marker device when the associated bone rigidly attached with the portable consumer electronic device by the template is pivoted about the center of rotation, wherein the template held in the predetermined spatial relationship on the bone of the associated patient defines the second point of the mechanical axis of the associated bone in the reference frame of the portable consumer electronic device, and wherein the control unit determines by the processor executing the computer program stored in the memory device, with the electronic device rigidly attached to the bone of the associated patient by the template held in the predefined spatial relationship on the second point, the mechanical axis of the associated bone as a line extending between the first point determined by the control unit from the output signal of the camera and the second point defined by the template held in the predetermined spatial relationship on the bone of the associated patient.

15. The system for determining a mechanical axis of a bone of an associated patient according to claim 14, further comprising:

at least one inertial sensor, wherein the camera, the at least one inertial sensor and the control unit are integrated into a common housing of the portable consumer electronic device.

16. The system for determining a mechanical axis of a bone of an associated patient according to claim 14, further comprising:

at least one inertial sensor, wherein the camera and the at least one inertial sensor are provided in a first housing of the portable consumer electronic device, wherein the control unit is provided in a second housing which is separate from the first housing of the portable consumer electronic device, wherein the system comprises a data transfer unit, operatively coupled to the processor, configured to transfer data from the camera and the at least one inertial sensor to the control unit.

17. The system for determining a mechanical axis of a bone of an associated patient according to claim 14, further comprising:

the associated stationary marker device, wherein the system for determining the mechanical axis of an associated bone in combination with the stationary marker device comprises a medical navigation system.

18. An apparatus for determining a mechanical axis of a bone having a surface, a part of the surface having a shape, the apparatus comprising:

a portable consumer electronic device comprising a camera, a non-transient memory device, and a processor operable to execute instructions stored in the non-transient memory device; and a template having a surface adapted to the shape of the part of the surface of the bone wherein the surface of the template has an inverse shape of the shape of the part of the surface of the bone, the template being selectively attachable onto the bone with the surface of the template having the inverse shape of the shape of the part of the surface of the bone being engaged with the shape of the part of the surface of the bone, and the template defining, when attached onto the bone, a second point of two points defining the mechanical axis of the bone, wherein the portable consumer electronic device is selectively positionable in aligned contact with the template attached with the bone, the portable consumer electronic device when positioned in the aligned contact with the template and with the template attached with the bone with the surface of the template having the inverse shape of the shape of the part of the surface of the bone being engaged with the shape of the part of the surface of the bone providing a defined spatial relationship in a reference frame of the portable consumer electronic device between the portable consumer electronic device and the second point defined by the template, wherein the camera, with the portable consumer electronic device being positioned in the aligned contact with the template and with the template attached with the bone with the surface of the template having the inverse shape of the shape of the part of the surface of the bone being engaged with the shape of the part of the surface of the bone, is operable to capture a plurality of images of an associated stationary marker while the bone is pivoted, wherein the processor is operable to execute the instructions stored in the non-transient memory device to determine, from the plurality of images captured during the pivoting, a center of rotation of the bone in the reference frame of the portable consumer electronic device, wherein the processor is operable to execute the instructions stored in the non-transient memory device to determine the first point of the two points as the determined center of rotation of the bone.

19. The apparatus according to claim 18, wherein the template is self-centering on the bone.

20. The apparatus according to claim 18, wherein the template defines an arrow having a tip, the tip of the arrow pointing to the second point of the two points defining the mechanical axis of the bone when the template is attached with the bone with the surface of the template having the inverse shape of the shape of the part of the surface of the bone being engaged with the shape of the part of the surface of the bone.

* * * * *